(12) United States Patent
Hanson et al.

(10) Patent No.: US 9,036,019 B2
(45) Date of Patent: *May 19, 2015

(54) FALL DETECTION AND REPORTING TECHNOLOGY

(71) Applicant: Alarm.com Incorporated, Vienna, VA (US)

(72) Inventors: Mark Andrew Hanson, Fairfax, VA (US); Jean-Paul Martin, Oakton, VA (US); Adam T. Barth, Annandale, VA (US); Christopher Silverman, Alexandria, VA (US)

(73) Assignee: Alarm.com Incorporated, Vienna, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/200,407

(22) Filed: Mar. 7, 2014

(65) Prior Publication Data

US 2014/0247335 A1 Sep. 4, 2014

Related U.S. Application Data

(63) Continuation of application No. 13/439,690, filed on Apr. 4, 2012, now Pat. No. 8,675,920.

(60) Provisional application No. 61/471,495, filed on Apr. 4, 2011.

(51) Int. Cl.
| | |
|---|---|
| H04N 7/18 | (2006.01) |
| G08B 21/04 | (2006.01) |
| A61B 5/11 | (2006.01) |
| G06K 9/00 | (2006.01) |
| A61B 5/00 | (2006.01) |

(52) U.S. Cl.
CPC ............ *G08B 21/043* (2013.01); *A61B 5/0077* (2013.01); *A61B 5/1117* (2013.01); *A61B 5/0022* (2013.01)

(58) Field of Classification Search
CPC .................................. A61B 5/00; G08B 21/00
USPC .......... 382/103, 107, 236; 348/152, 154, 155, 348/169, 170, 171, 172, 208.16, 352, 77
See application file for complete search history.

(56) References Cited

U.S. PATENT DOCUMENTS

| | | | | |
|---|---|---|---|---|
| 8,106,782 | B2* | 1/2012 | Fredriksson et al. | 340/573.4 |
| 8,675,920 | B2* | 3/2014 | Hanson et al. | 382/103 |
| 2008/0129518 | A1* | 6/2008 | Carlton-Foss | 340/573.1 |
| 2009/0278934 | A1* | 11/2009 | Ecker et al. | 348/152 |

* cited by examiner

*Primary Examiner* — Abolfazl Tabatabai
(74) *Attorney, Agent, or Firm* — Fish & Richardson P.C.

(57) ABSTRACT

Fall detection and reporting technology, in which output from at least one sensor configured to sense, in a room of a building, activity associated with a patient falling is monitored and a determination is made to capture one or more images of the room based on the monitoring. An image of the room is captured with a camera positioned to include the patient within a field of view of the camera and the captured image of the room is analyzed to detect a state of the patient at a time of capturing the image. A potential fall event for the patient is determined based on the detected state of the patient and a message indicating the potential fall event for the patient is sent based on the determination of the potential fall event for the patient. Techniques are also described for fall detection and reporting using an on-body sensing device.

20 Claims, 12 Drawing Sheets

FALL DETECTION AND REPORTING TECHNOLOGY

CROSS REFERENCE TO RELATED APPLICATIONS

This application is a continuation (and claims the benefit of priority under 35 USC 120) of U.S. application Ser. No. 13/439,690, filed Apr. 4, 2012, now allowed, which claims the benefit to U.S. Provisional Application No. 61/471,495, filed Apr. 4, 2011, each of which is incorporated herein by reference in its entirety for all purposes.

TECHNICAL FIELD

This disclosure relates to fall detection and reporting technology.

BACKGROUND

Falls are a public health concern and cause for institutionalization in the senescent population, for whom they disproportionately affect. Loosely defined as an unintentional and uncontrolled movement towards the ground or lower level, a fall can have debilitating and sometimes fatal consequences. Although falls increase rates of morbidity and mortality, earlier detection and reporting of such events can improve outcomes.

Practical, early detection and reporting of falls has been an elusive goal. Efforts to detect falls have classically employed wearable technologies to capture user input (e.g., panic button press) or to characterize and classify movements and postures. Although these technologies demonstrate reasonable utility in ideal conditions, user non-compliance and fall-related incapacitation reduce general efficacy in application. Furthermore, inability to verify incidence of detected falls (e.g., both true and false) leads to inaccurate fall reporting and undesirable handling of potential fall events.

SUMMARY

Techniques are described for fall detection and reporting technology. In one aspect, a method includes monitoring output from at least one sensor configured to sense, in a room of a building, activity associated with a patient falling and, based on the monitoring of output from the at least one sensor, determining to capture one or more images of the room. The method also includes capturing, with a camera positioned to include the patient within a field of view of the camera, an image of the room and analyzing the captured image of the room to detect a state of the patient at a time of capturing the image. The method further includes determining, based on the detected state of the patient, a potential fall event for the patient and, based on the determination of the potential fall event for the patient, sending, by a communication device, a message indicating the potential fall event for the patient.

Implementations may include one or more of the following features. For example, the at least one sensor configured to sense activity associated with the patient falling may be an on-body sensor configured to detect an impact and determine a change in an orientation of the patient. In this example, the method may include receiving data indicating a detected change in an orientation of the patient and an amount of the orientation change, receiving data indicating a detected impact and a severity of the detected impact, and determining, based on the received amount of orientation change and the received data indicating the severity of the impact of the patient, a threshold for inactivity of the patient. The method also may include determining, based on output from the on-body sensor, that the patient has been inactive for a period of time greater than the determined threshold and determining to capture one or more images of the room based on the determination that the patient has been inactive for a period of time greater than the determined threshold.

In addition, the at least one sensor configured to sense activity associated with the patient falling may be a button located in the room at a position that permits the patient to press the button after a fall and the method may include determining that the button has been pressed. The at least one sensor configured to sense activity associated with the patient falling may be a sensor configured to determine a presence of the patient in the room and the method may include receiving, from the sensor configured to determine the presence of the patient in the room, a signal indicating that the patient is present in the room and, after a threshold period of time, determining that the patient has not left the room and that no further signals have been received from the sensor configured to determine the presence of the patient in the room. The method may include determining to capture one or more images of the room based on determining that the patient has not left the room and that no further signals have been received from the sensor configured to determine the presence of the patient in the room.

In some examples, the method may include performing image foreground segmentation on the captured image to create a segmented image, performing template matching on the segmented image to identify a human shape in the segmented image, and calculating a position and an orientation associated with the identified human shape in the segmented image. In these examples, the method may include determining a potential fall event for the patient based on the calculated position and the calculated orientation. Further, in these examples, the method may include monitoring successive image and sensor data after calculating the position and the orientation, comparing the successive image and sensor data with prior image and sensor data, determining an activity level of the patient based on the comparison of the successive image and sensor data with the prior image and sensor data, classifying the potential fall event based on the determined activity level of the patient, and handling reporting for the potential fall event based on the classification of the potential fall event.

In some implementations, the method may include analyzing the monitored output from the at least one sensor over a period of time to determine activities of the patient over the period of time and accessing information indicative of expected activities of the patient over the period of time. In these implementations, the method may include comparing the determined activities of the patient over the period of time to the expected activities of the patient over the period of time and, based on the comparison revealing that the determined activities of the patient over the period of time do not match the expected activities of the patient over the period of time, determining a level of fall risk associated with the patient.

The method may include determining that the level of fall risk associated with the patient exceeds a threshold and, based on the determination that the level of fall risk associated with the patient exceeds the threshold, sending a message to a monitoring server that is located remotely from the building. The method also may include determining that the level of fall risk associated with the patient exceeds a threshold and, based on the determination that the level of fall risk associated with the patient exceeds the threshold, automatically performing one or more operations to reduce the level of fall risk associated with the patient.

In some examples, the method may include sending, to the patient, the message indicating the potential fall event and providing the patient with an opportunity to cancel the potential fall event. In these examples, the method may include determining that the patient has not cancelled the potential fall event within a threshold period of time and, based on determining that the patient has not cancelled the potential fall event within the threshold period of time, sending a message to a monitoring server indicating the potential fall event. Further, in these examples, the method may include receiving, from the patient, an indication to cancel the potential fall event and, based on receiving the indication to cancel the potential fall event, determining an overall activity of the patient between detecting the potential fall event and receiving the indication to cancel the potential fall event.

In addition, the method may include determining that the overall activity of the patient is above a threshold of activity and, based on determining that the overall activity of the patient is above the threshold of activity, signaling that the potential fall event was detection of a false fall. The method also may include determining that the overall activity of the patient is below a threshold of activity and, based on determining that the overall activity of the patient is below the threshold of activity, determining an orientation of the patient. The method further may include determining that the determined orientation of the patient is upright and, based on determining that the determined orientation of the patient is upright, signaling that the potential fall event was detection of a minor fall.

In some implementations, the method may include determining that the determined orientation of the patient is not upright and, based on determining that the determined orientation of the patient is not upright, sending another message to the patient that provides the patient with another opportunity to cancel the potential fall event. In these implementations, the method may include determining that the patient has not cancelled the potential fall event within a threshold period of time after sending another message to the patient that provides the patient with another opportunity to cancel the potential fall event and, based on determining that the patient has not cancelled the potential fall event within the threshold period of time after sending another message to the patient that provides the patient with another opportunity to cancel the potential fall event, sending a message to a monitoring server indicating the potential fall event. Also, in these implementations, the method may include after sending another message to the patient that provides the patient with another opportunity to cancel the potential fall event, receiving, from the patient, an indication to cancel the potential fall event and, based on receiving the indication to cancel the potential fall event, signaling that the potential fall event was a cancelled fall event.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Techniques are described for addressing the aforementioned fall detection and reporting challenges. For example, a monitoring system in a premise performs fall detection and reporting operations based on output from a sensor (e.g., an image sensor). When the monitoring system detects that a person has fallen in the premise, actions are taken to assist the fallen person.

Figure 1:
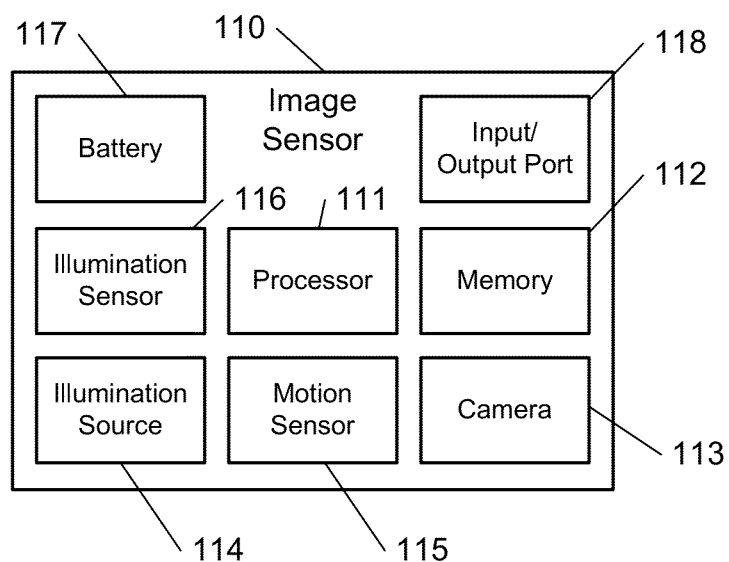
FIGS. 1, 2, and 4 to 6 illustrate example systems.

FIG. 1 illustrates an image sensing device 110 that may be installed within a monitored home or facility. The image sensing device 110 combines multi-modal sensing (e.g., passive infrared motion sensor, triaxial inertial sensor, illumination sensor), an infrared illumination source, camera, processor, memory, battery, and input/output capabilities. The image sensing device 110 detects events indicative of potential falls proximal to its installation location. A plurality of image sensing devices can be installed throughout a home or facility, and used in conjunction with other sensors, to increase the fall detection coverage area and provide specific location information for fall reporting and response.

The image sensing device 110 includes a processor 111, a memory 112, a camera 113, an illumination source 114, a motion sensor 115, an illumination sensor 116, a battery 117, and an input/output port 118. The processor 111 controls operations of the image sensing device 110 and may be any suitable processor. The memory 112 stores instructions that are executed by the processor 111 and also stores images captured by the camera 113. The memory 112 may be any type of memory that is capable storing data and may include a combination of multiple, memory units. For example, the memory 112 may be a Flash memory component that stores both instructions that are executed by the processor and images captured by the camera 113.

The camera 113 captures images of an area proximate to where the image sensing device is located. For instance, the camera 113 may be placed at an upper corner of a room in a building and, in this instance, the camera 113 captures images of the room. The camera 113 may be a video/photographic camera or other type of optical sensing device configured to capture images. In some implementations, the camera 113 is a CMOS camera sensor (or other CCD sensor) that captures images at various, different resolutions (e.g., low and/or high resolutions). For instance, the CMOS camera sensor may capture 640×480 pixels (e.g., VGA resolution) or higher resolutions. The camera 113 also may capture a lower resolution image (e.g., Quarter VGA=QVGA=320×240 pixels).

The illumination source 114 may be any source of illumination that improves capturing of images in a dark area. For example, the illumination source 114 may include one or more Infra Red LEDs that emit Infra Red light over an area within a field of view of the camera 113 to illuminate objects within the area. The processor 111 may control the illumination source 114 to emit light when the illumination sensor 116 detects a level of light that is below a threshold level.

The motion sensor 115 may be Passive Infra Red (PIR) motion sensor, a microwave motion sensor, or any type of sensor that detects motion in an area corresponding to a field of view of the camera 113. The processor 111 may monitor output of the motion sensor 115 and trigger the camera 113 to capture images in response to the motion sensor 115 detecting motion in the area corresponding to the field of view of the camera 113.

The battery 117 is the power source of the image sensing device 110 and may be any type of battery capable of delivering power to the image sensing device 110. The battery 117 may have a relatively small size and may be a standard type of battery available for purchase at retail stores. The battery 117 may be located in a compartment that is easily accessible to a user of the image sensing device 110 to facilitate changing of the battery 117, which may occur relatively frequently (e.g., every couple of months) depending on the power consumption and image capture settings of the image sensing device 110.

The input/output port 118 is a communication interface through which the image sensing device may send and receive wireless communications. The input/output port 118 may, using a short range wireless protocol (e.g., Bluetooth, Z-Wave, ZigBee, local wireless 900 MHz communication band, etc.), receive and send short range wireless communications with other devices. The input/output port 118 may include a "normally open" or "normally closed" digital input that can trigger capture of images using the camera 113.

To reduce processing power needed and to conserve battery life, the processor 111 may control components of the image sensing device 110 to periodically enter sleep mode operation. For example, the processor 111 may awaken every second to determine whether any communications have been received at the input/output port 118. If no communications have been received, the processor 111 may place itself and other components (e.g., the memory 112, the camera 113, etc.) in a sleep mode for another second before awaking again to determine whether any communications have been received at the input/output port 118. The processor 111 also may awaken from a sleep mode state based on output from the motion sensor 115 indicating that motion has been detected and/or based on output from an "inertial sensor" that detects impacts to the image sensing device 110.

Figure 2:
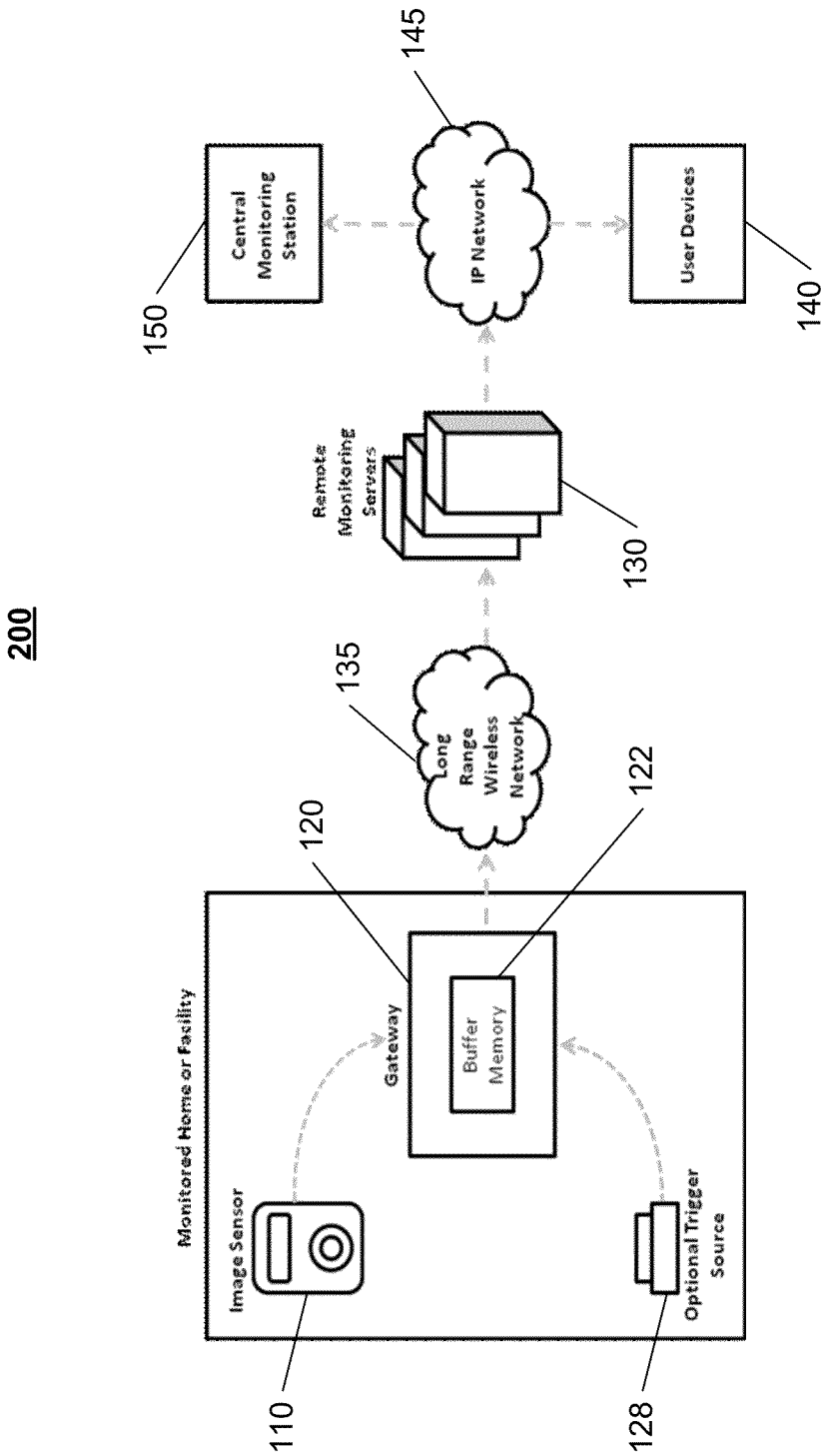

FIG. 2 illustrates an example of an electronic system 200 configured to provide fall detection and reporting. The system 200 includes the image sensing device 110, a gateway 120, one or more remote monitoring servers 130, one or more user devices 140, and a central monitoring station 150. The image sensing device 110 is a relatively small and affordable unit that captures still images of an area that corresponds to a location of the image sensing device. Because the image sensing device 110 is relatively small, runs off of battery power, and communicates via a wireless communication protocol, the image sensing device 110 may be easily placed at any location within a monitored property (or just outside of a monitored property) to provide image surveillance of an area of the monitored property (or an area just outside of the monitored property).

The gateway 120 is a communication device configured to exchange short range wireless communications with the image sensing device 110 and long range wireless or wired communications with the remote monitoring server 130 over the network 135. Because the gateway 120 exchanges short range wireless communications with the image sensing device 110, the gateway 120 is positioned nearby the image sensing device 110. As shown in FIG. 2, the gateway 120 and the image sensing device 110 are both located within a monitored property that is remote (and may be very far away from) the remote monitoring server 130.

In some examples, the gateway 120 may include a wireless communication device configured to exchange long range communications over a wireless data channel. In this example, the gateway 120 may transmit header data and image data over a wireless data channel. The gateway 120 may include one or more of a GSM module, a radio modem, cellular transmission module, or any type of module configured to exchange communications in one of the following formats: GSM or GPRS, CDMA, EDGE or EGPRS, EV-DO or EVDO, or UMTS.

The gateway 120 includes a buffer memory 122 that stores image data captured by the image sensing device 110. The buffer memory 122 may temporarily store image data captured by the image sensing device 110 to delay a decision of whether the image data (or a subset of the image data) is worthwhile to send to the remote monitoring server 130. The buffer memory 122 may be larger than the memory 112 of the image sensing device 110 and, because the gateway 120 operates using an AC power source, using the buffer memory 122 to store images captured by the image sensing device 110 may be more efficient. The gateway 120 also may include a display with which the stored images may be displayed to a user.

The long range wireless network 135 enables wireless communication between the gateway 120 and the remote monitoring server 130. The long range wireless network 135 may be any type of cellular network and may support any one or more of the following protocols: GSM or GPRS, CDMA, EDGE or EGPRS, EV-DO or EVDO, or UMTS. It may be relatively expensive to transmit data over the long range wireless network 135 and, therefore, the image sensing device 110 and the gateway 120 may be selective in the image data transmitted to the remote monitoring server 130.

The remote monitoring server 130 receives image data from the gateway 120 over the long range wireless or wired network 135. The remote monitoring server 130 stores the received image data and makes the image data available to one or more user devices 140 and/or the central monitoring station 150 over the IP-based network 145. For instance, the remote monitoring server 130 may make the image data available to the one or more user devices 140 and/or the central monitoring station 150 at a website accessible by the one or more user devices 140 and/or the central monitoring station 150 over the Internet. The remote monitoring server 130 also may make the image data available to the one or more user devices 140 and/or the central monitoring station 150 in an electronic message, such as an electronic mail message.

In some implementations, the remote monitoring server 130 receives the image data from the gateway 120 as a reference image and a series of differential images that indicate the difference between the corresponding image and the reference image. In these implementations, header information sent with the image data indicates which images are reference images, which images are differential images, and which reference image each differential image corresponds to. The remote monitoring server 130 processes the reference image and the differential images and converts each image into a standard image format, such as JPEG. The remote monitoring server 130 then stores the converted images in a database or a file system and makes the converted images available to the one or more user devices 140 and/or the central monitoring station 150.

The central monitoring station 150 includes an electronic device (e.g., a server) configured to provide alarm monitoring service by exchanging communications with the remote monitoring server 130 over the network 145. For example, the central monitoring station 150 may be configured to monitor alarm events generated by a monitoring or alarm system that monitors the home or facility where the image sensing device 110 is located. In this example, the central monitoring station 150 may exchange communications with the remote monitoring server 130 to receive information regarding alarm events detected by the monitoring or alarm system. The central monitoring station 150 also may receive information regarding alarm events from the one or more user devices 140. The central monitoring station 150 may receive images captured by the image sensing device 110 to enable verification of potential fall events.

The central monitoring station 150 may be connected to multiple terminals. The terminals may be used by operators to process alarm events. For example, the central monitoring station 150 may route alarm data to the terminals to enable an operator to process the alarm data. The terminals may include general-purpose computers (e.g., desktop personal computers, workstations, or laptop computers) that are configured to receive alarm data from a server in the central monitoring station 150 and render a display of information based on the alarm data. For example, the central monitoring station 150 may receive alarm data and route the alarm data to a terminal for processing by an operator associated with the terminal. The terminal may render a display to the operator that includes information associated with the alarm event (e.g., the name of the user of the alarm system, the address of the building the alarm system is monitoring, the type of alarm event, images of fall events taken of the image sensing device 110, etc.) and the operator may handle the alarm event based on the displayed information.

The one or more user devices 140 include devices that host user interfaces. For instance, the user devices 140 may include a mobile device that hosts one or more native applications (e.g., a fall detection and reporting application). The user devices 140 may include a cellular phone or a non-cellular locally networked device with a display. The user devices 140 may include a smart phone, a tablet PC, a personal digital assistant ("PDA"), or any other portable device configured to communicate over a network and display information. For example, implementations may also include Blackberry-type devices (e.g., as provided by Research in Motion), electronic organizers, iPhone-type devices (e.g., as provided by Apple), iPod devices (e.g., as provided by Apple) or other portable music players, other communication devices, and handheld or portable electronic devices for gaming, communications, and/or data organization. The user devices 140 may perform functions unrelated to the monitoring system, such as placing personal telephone calls, playing music, playing video, displaying pictures, browsing the Internet, maintaining an electronic calendar, etc.

The user devices 140 may include a native fall detection and reporting application. The native fall detection and reporting application refers to a software/firmware program running on the corresponding mobile device that enables the user interface and features described throughout. The user devices 140 may load or install the native fall detection and reporting application based on data received over a network or data received from local media. The native fall detection and reporting application runs on mobile device platforms, such as iPhone, iPod touch, Blackberry, Google Android, Windows Mobile, etc. The native fall detection and reporting application enables the user devices 140 to receive and process image and sensor data from the monitoring system.

The user devices 140 also may include a general-purpose computer (e.g., a desktop personal computer, a workstation, or a laptop computer) that is configured to communicate with the remote monitoring server 130 over the network 145. The user devices 140 may be configured to display a fall detection and reporting user interface that is generated by the user devices 140 or generated by the remote monitoring server 130. For example, the user devices 140 may be configured to display a user interface (e.g., a web page) provided by the remote monitoring server 130 that enables a user to perceive images captured by the image sensing device 110 and/or reports related to the monitoring system.

The system 200 further includes one or more trigger sources 128. The trigger sources 128 may include devices that assist in detecting fall events. For example, the trigger sources 128 may include contact or pressure sensors that are positioned at a lower part of a building (e.g., at or near the floor). In this example, when a person falls, the person may touch one of the trigger sources 128 to alert the system 200 to the fall. In this regard, the system 200 may use output of the trigger sources 128 to identify a possible fall location and begin capturing and processing images near that location to determine whether the trigger relates to an actual fall event or a false alarm, such as inadvertent contact with a trigger source.

In some examples, the system 200 may include inertial sensors (e.g., accelerometers) to detect an impact potentially generated from a fall. In these examples, when a person falls, the inertial sensors may detect an impact and the system 200 may use the detected impact to infer a potential fall. In this regard, the system 200 may use output of the inertial sensors to identify a possible fall location and begin capturing and processing images near that location to determine whether the detected impact relates to an actual fall event or a false alarm, such as dropping of an object that resulted in the detected impact.

In some implementations, the image sensing device 110 and the gateway 120 may be part of a home or facility monitoring system (e.g., a home security system). In these implementations, the home or facility monitoring system may sense many types of events or activities associated with the home or facility and the sensed events or activities may be leveraged in performing fall detection and reporting features. The home or facility monitoring system may include a controller that communicates with the gateway 120. The controller may be configured to control the home or facility monitoring system (e.g., a home alarm or security system). In some examples, the controller may include a processor or other control circuitry configured to execute instructions of a program that controls operation of an alarm system. In these examples, the controller may be configured to receive input from sensors, detectors, or other devices included in the home or facility monitoring system and control operations of devices included in the home or facility monitoring system or other household devices (e.g., a thermostat, an appliance, lights, etc.).

The home or facility monitoring system also includes one or more sensors or detectors. For example, the home or facility monitoring system may include multiple sensors, including a contact sensor, a motion sensor, a glass break sensor, or any other type of sensor included in an alarm system or security system. The sensors also may include an environmental sensor, such as a temperature sensor, a water sensor, a rain sensor, a wind sensor, a light sensor, a smoke detector, a carbon monoxide detector, an air quality sensor, etc. The sensors further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, bathroom usage sensors, food consumption sensors, etc. In some examples, the sensors 120 may include a radio-frequency identification (RFID) sensor that identifies a particular article that includes a pre-assigned RFID tag.

Figure 3:
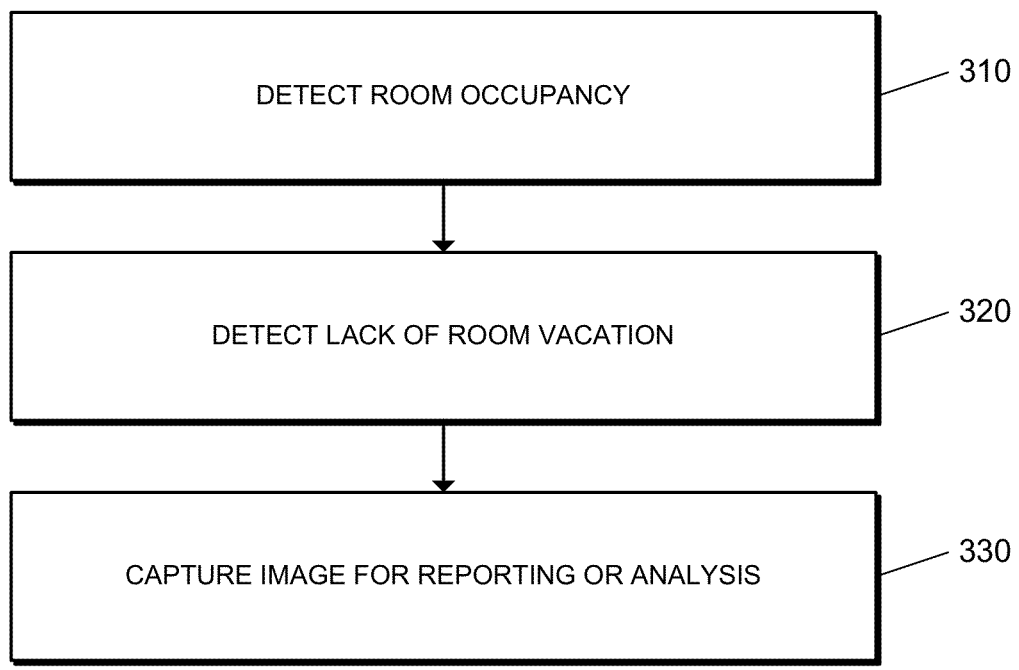
FIGS. 3, 7, 8, 10, and 11 are flow charts illustrating example processes.
Figure 4:
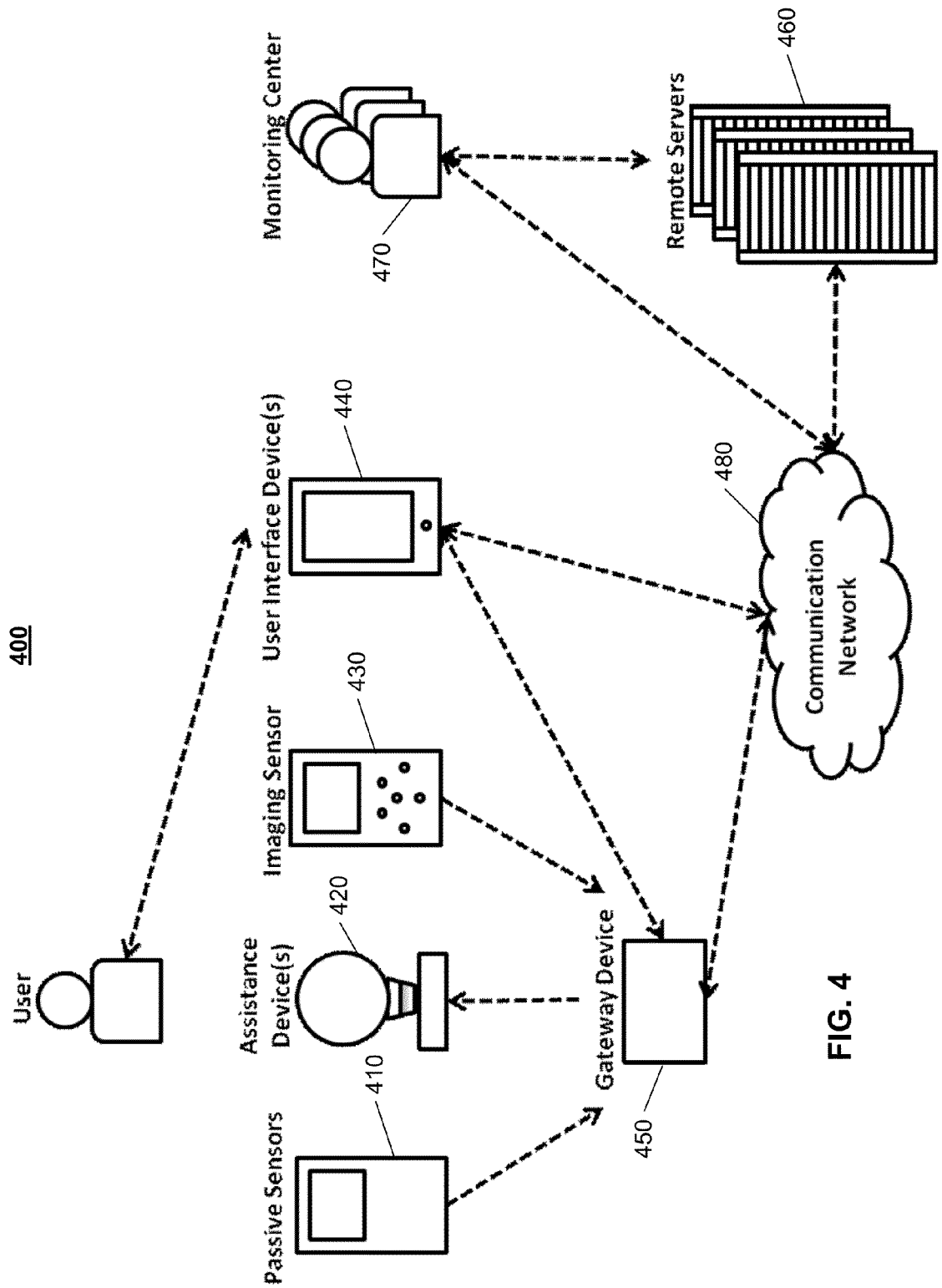

The system 200 shown in FIG. 2 may be used for the two example processes 300 and 400 of fall detection and reporting described with respect to FIGS. 3 and 4. The example processes 300 and 400 are independent; however, they can be staged so that first level fall detection triggers further (e.g., second level) analysis and classification of potential fall events. Both processes 300 and 400 have multiple steps, although a subset of steps may be employed to still meet practical requirements of fall detection and reporting.

FIG. 3 illustrates an example process 300 for fall detection and reporting. The operations of the example process 300 are described generally as being performed by the system 200. The operations of the example process 300 may be performed by one of the components of the system 200 (e.g., the image sensing device 110, the gateway 120, the remote monitoring server 130, etc.) or may be performed by any combination of the components of the system 200. In some implementations, operations of the example process 300 may be performed by one or more processors included in one or more electronic devices.

In general, the process 300 enables fall detection and reporting based on room occupancy analysis. The system 200 detects room occupancy (310). For example, movement events may be detected by the image sensing device or other external sensors (e.g., perceived motion by passive infrared motion sensor of the image sensing devices, door openings and closings detected by door/window contact sensors of a home security system). In this example, the movement events signal possible human entrance into a room where the image sensing device is located and are used to detect room occupancy. The system 200 may capture camera image(s) and analyze the camera image(s) to verify that the room is occupied.

After detecting room occupancy, the system 200 detects a lack of room vacation (320). For example, the system 200 monitors output of the image sensing device or other external sensors for movement events in the occupied room and other rooms in the property. In this example, the system 200 detects successive movement events based on sensors of the image device or other external sensors (even in other rooms). The successive movement events signal human vacation of the room and the system 200 analyzes the successive movement events to determine whether the room has been vacated. For instance, the system 200 may determine that the room has been vacated when no successive movement events are detected in the room and successive movement events are detected in other rooms of the property. The system 200 may determine that the room has not been vacated when successive movement events are detected in the room and/or no successive movement events are detected in other rooms of the property. Based on a determination that the room has been vacated, the system 200 ceases further analysis and does not perform fall detection processing for the room until the room is detected as being occupied again.

Based on a determination that the room remains occupied, the system 200 captures one or more images for analysis and/or reporting (330). For instance, if sensors indicate that the room remains occupied, but further movement has ceased over a prescribed and configurable interval of time, the system 200 initiates image capture for reporting, further assessment, and/or validation of the possible fall event.

FIG. 4 illustrates another example of an electronic system 400 configured to provide fall detection and reporting. The system 400 includes one or more passive sensors 410, one or more assistance devices 420, one or more imaging sensors 430, one or more user interface devices 440, a gateway device 450, one or more remote servers 460, and a monitoring center 470. The one or more user interface devices 440, the gateway device 450, the one or more remote servers 460, and the monitoring center 470 may exchange communications over a communication network 480.

Passive sensors 410 may be employed to measure activity or inactivity within a monitored residence. The activity or inactivity can be associated with a fall (e.g., impact, period of inactivity, location, time, etc.) or it can measure aspects of behavior related to fall risk (e.g., general activity level, sleeping, eating, bathroom use, medication use, gait speed, etc.). The behavior profiling can help to promote fall risk reduction via automated assistance devices 420 or through behavior change suggestions via user interface device(s) 440.

Assistance devices 420 are capable of performing automated tasks based on inputs from sensors 410, a gateway device 450, user interface device(s) 440, or remote servers 460. Assistance devices 420 can be programmed to respond based on rules specified by users, by caregivers, or by default. For example, a light can be illuminated in response to a bed sensor being vacated during the evening. Assistance devices 420 can also report their state to other devices, systems, or stakeholders.

Imaging sensors 430 (e.g., still frame or video) are capable of detecting possible falls. Furthermore, imaging sensors 430 can forward images of possible falls to remote servers 460, caregivers, or monitoring centers 470 for automated or human verification. Imaging sensors 430 may also have other modes of sensing (e.g., motion, acceleration, etc.) to trigger or augment native imaging and sensing capabilities. For example, impact sensed by the image sensor 430 could be used to trigger image capture. Captured images, sensed data, or other information (e.g., location, time, etc.) may be communicated to other devices, systems, or stakeholders.

In some implementations, the image sensing device 110 described above with respect to FIG. 1 may be used as the imaging sensors 430. The image sensing device 110 may be installed within a monitored home or facility. The device 110 combines multi-modal sensing (e.g., passive infrared motion sensor, triaxial inertial sensor, illumination sensor), an infrared illumination source, camera, processor, memory, battery, input/output, and radio (e.g., via input/output) capabilities. The device 110 detects events indicative of potential falls proximal to its installation location. A plurality of devices 110 may be installed throughout a home or facility, and used in conjunction with other sensors, to increase the fall detection coverage area and provide specific location information for fall reporting and response.

A user interface device 440 may be used to communicate information to or gather information from a user about activity related to fall prevention, fall detection, or daily living. Possible physical incarnations of user interface devices 440 may include light or audio sources, displays, push buttons, or mobile devices (e.g., mobile phones or mobile phone applications). A user interface device 440 may also act as a sensing device and relay data to a gateway device 450 or directly to remote servers 460 through the communication network 480.

Figure 5:
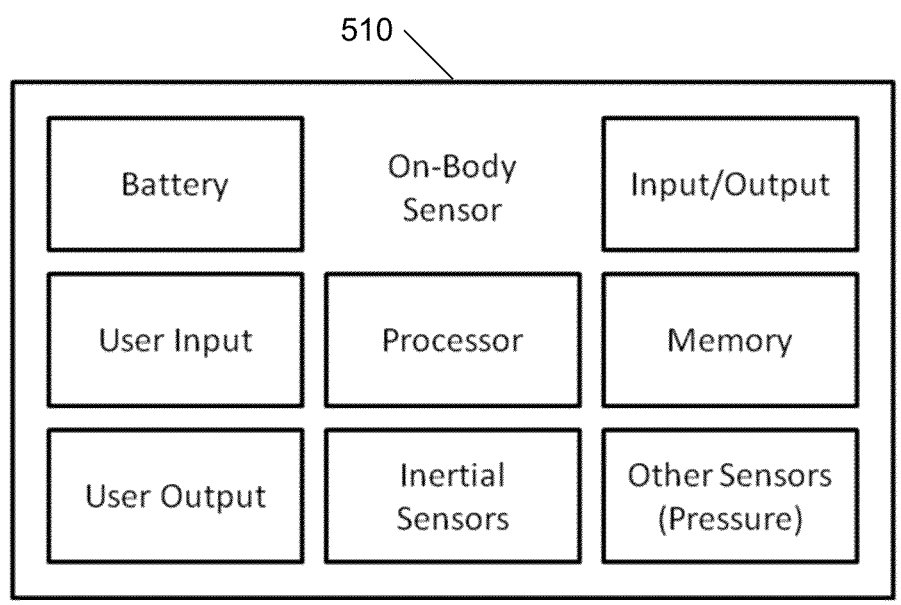

FIG. 5 illustrates an example of a user interface and sensing device. Specifically, FIG. 5 illustrates an on-body sensor 510. The on-body sensor 510 may be a fall and movement sensor with an emergency button. The on-body sensor 510 is intended to be worn and easily attached to many articles of clothing on the trunk (e.g., belt, lapel, brazier, lanyard, etc.).

Figure 6:
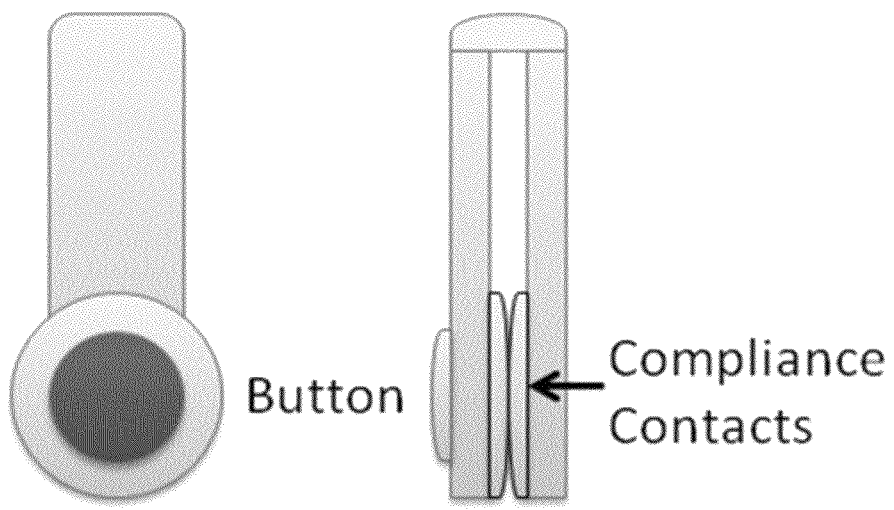

FIG. 6 illustrates a device 600 that represents an example of the on-body sensor 510. In order to facilitate wearability, the device 600 embodies a clip form factor. The clip is fastened closed through tension when no force is applied, but can be opened upon demand (e.g., similar to a clothes pin), thereby ensuring that it remains connected to an article of clothing.

When no force is applied to the clip, both sides of the device 600 are in contact with one another. The device 600 includes compliance contacts (e.g., an electrical switch) comprising a conductive contact on each side of the clip. When the clip is forced open or clipped around a piece of fabric, the switch is opened. Otherwise, the switch is closed and the circuit loop completed. Using the compliance contacts, the system 400 can identify whether the sensor is being worn. This information can be used to identify false falls created from dropping or otherwise handling the device 600 when not worn. The user can also be reminded via audible or visual interfaces based on the system 400 detecting that the device 600 is not being worn as a result of the output of the compliance contacts. In determining whether to provide the reminder, the system 400 may consider other sensors within the monitored premise. For instance, the system 400 may detect motion within the monitored premise based on output of one or more motion sensors, determine that the device 600 is not being worn based on output from the compliance contacts, and provide a reminder to wear the device 600 based on the determination that the device 600 is not being worn at a time when motion has been detected in the monitored premise.

Referring again to FIG. 5, the on-body sensor 510 comprises multi-modal sensing (e.g., triaxial inertial sensor, angular rate sensor, magnetometer, barometric pressure sensor, etc.), input/output, radio (e.g., via input/output), a processor, memory, battery, and user interface capabilities for human interaction (e.g., a button, LED/LCD, buzzer, etc.). The on-body sensor 510 may be used to measure gross human motion and activity, detect specific events or behaviors (e.g., falls, walking, running, sleeping, etc.), communicate to the user (e.g., reminders, notifications, etc.), or capture user input (e.g., panic button press, verification of event, etc.). Detecting falls with on-body sensing is described in further detail below.

Referring again to FIG. 4, a gateway device 450 can be used to relay information between remote servers 460 (e.g., over public or private communication network) and systems at the user location. The gateway device 450 can also allow systems within a user's location to communicate without involvement from remote servers 460. Certain incarnations of the system 400 may not include a gateway device 450. Therefore, passive sensors 410, assistance devices 420, imaging sensors 430, and/or user interface devices 440 may be connected directly to the communication network 480.

Remote servers 460 may be employed to store, process, and initiate actions based upon fall, fall-related, or other data collected about each monitored user and location. Monitoring center agents can also annotate user records stored on the remote servers 460.

A monitoring center 470 may employ automated or human agents to observe users' fall-related events and contact users or caregivers based on defined protocols, quantitative or qualitative assessments. Monitoring center agents can also annotate user records stored on the remote server 460.

Figure 7:
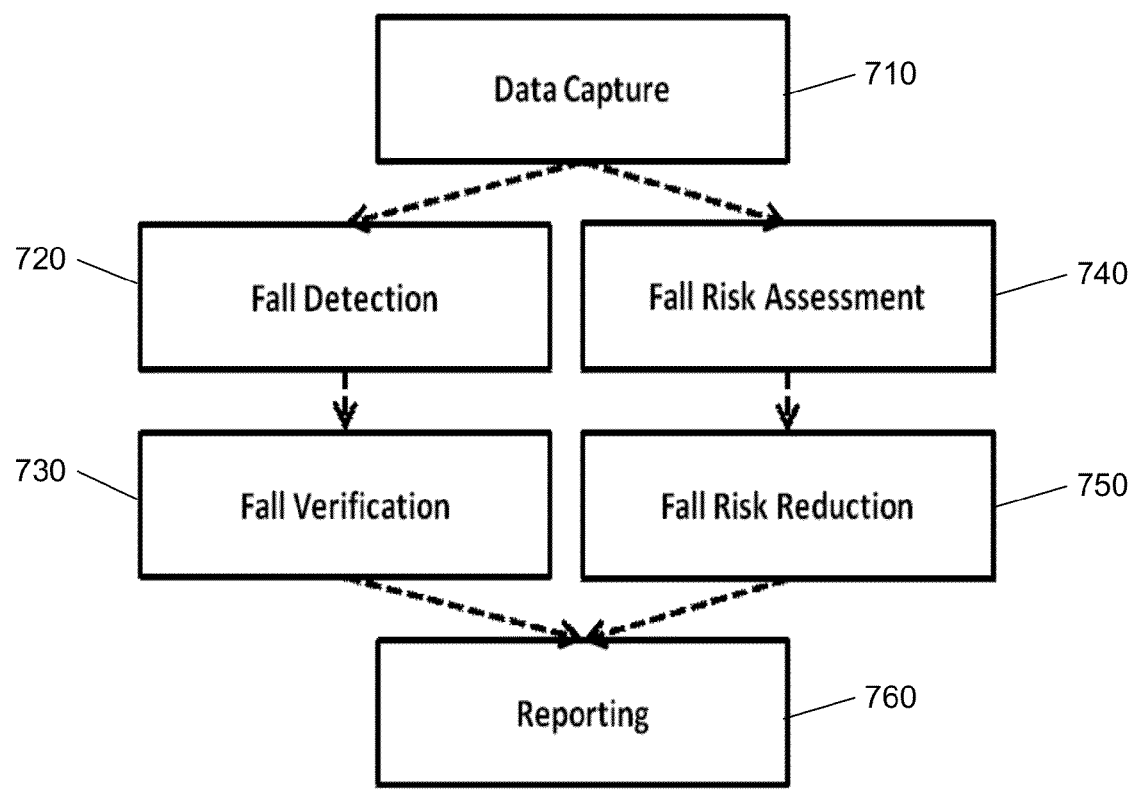

FIG. 7 illustrates an example process 700 for fall management. The operations of the example process 700 are described generally as being performed by the system 400. The operations of the example process 700 may be performed by one of the components of the system 400 or may be performed by any combination of the components of the system 400. The operations of the example process 700 also may be performed by one of the components of the system 200 or may be performed by any combination of the components of the system 200. In some implementations, operations of the example process 700 may be performed by one or more processors included in one or more electronic devices.

The fall management process 700 includes data capture (710), fall detection (720), fall verification (730), fall risk assessment (740), fall risk reduction (750), and reporting (760). Although several steps are illustrated as part of the fall management process 700, some fall management implementations may only employ a subset of these steps.

The system 400 performs data capture (710). Data can be captured from one or more passive sensors, imaging sensors, assistance devices, and user interface devices. Data can be unprocessed sensor readings or sensor-processed readings. Data capture can be triggered by the passive sensors, imaging sensors, user interface devices, remote servers, or monitoring center. Data capture can consist of instantaneous or continuously sampled readings. Data can be forwarded directly from devices to remote servers or to remote servers via a gateway device. Remote servers, a gateway device, or sensors may coordinate the capture of data or buffer data to facilitate on-sensor, on-gateway, or remote processing. In addition to raw sensor readings, meta-data encompassing sensor location, timestamp, etc. can be forwarded to other devices, sensors, gateways, or remote servers.

The system 400 performs fall detection (720). Falls can be detected independently by passive sensors, imaging sensors, or user interface devices (e.g., on-body sensor). Each device can classify a possible fall and communicate fall events or quantitative metrics related to the possibility of a fall (e.g., fall classification score). For example, an on-body sensor can capture human motion and detect motion characteristics indicative of a fall (described in more detail below). Furthermore, an image sensor can detect the likelihood of a fall through analysis of images and other in-device sensors (described in more detail below).

Fall detection may also be accomplished through the use of multiple sensors in parallel (e.g., hierarchical) or sequentially to improve sensitivity and specificity of fall detection. Numerous examples of combined sequential and parallel fall detection may be used and data from any combination of the sensors described throughout this disclosure may be fused and considered in combination to detect a potential fall event. For example, the system 400 may detect entry into a room based on output from a motion sensor and/or a door sensor. In this example, the system 400 detects that the room has not been exited after a threshold period of time has passed since the room entry was detected and detects sensor inactivity across all sensors after the room entry was detected. Based on the detections made and consideration of output of all of the sensors within the system 400, the system 400 determines that a potential fall event may have occurred in the room and, in response to the determination that a potential fall event may have occurred in the room, initiates further processing to verify whether a potential fall event has occurred in the room.

In another example, the system 400 detects a potential fall event based on output from an on-body sensor. In this example, the system 400 controls an imaging sensor to capture one or more images in a room where the potential fall event is expected to have occurred, performs analysis of the captured images, and detects possible presence of a prone individual on the ground in the room. The system 400 also detects sensor inactivity across all sensors after detecting the potential fall event based on output from the on-body sensor. Based on the detections made and consideration of output of all of the sensors within the system 400, the system 400 determines that a potential fall event may have occurred in the room and, in response to the determination that a potential fall event may have occurred in the room, initiates further processing to verify whether a potential fall event has occurred in the room.

Independent fall detection processes on single devices or groups of devices also may be weighted (e.g., based on confidence or accuracy of fall detection efficacy). Such weighting may be used to compute an aggregate score indicative of the confidence of a possible fall. Weights may be assigned based on currently observed data and conditions, historic data from the monitored individual, or population data. Fall detection sensitivity may be configured by the user based on manipulation of weights associated with any of the aforementioned steps. For example, fall sensitivity could be set by adjusting the interval of sensed inactivity or the threshold for decreased activity. The system 400 may consider output from any of the sensors in the system 400 in computing the aggregate score. The system 400 may use the aggregate score to detect a potential fall event by comparing the aggregate score to a threshold. For instance, the system 400 detects a potential fall event based on the comparison of the aggregate score to the threshold revealing that the aggregate score meets the threshold and determines that a potential fall event has not occurred based on the comparison of the aggregate score to the threshold revealing that the aggregate score does not meet the threshold. By considering weighted output from many different sensors and fall detection processes in computing the aggregate score, the system 400 may provide more accurate fall detection with a lower false positive rate because detection of a fall detection only occurs when several sensors sense potential fall criteria or a single sensor detects a very high likelihood of a potential fall.

The system 400 performs fall verification (730). If a likely fall is detected, the detecting device, gateway, remote server, or monitoring center can initiate fall verification. The process can include an automated or human-prompted user response. For example, a user may be alerted (e.g., by audible tone, vibration, human operator, automated operator, or visual indicator) to verify their need for help (e.g., a button press or vocal response) or may be alerted to respond within a period of time to cancel a potential fall event. A human operator may also speak and listen to a user over two-way communication link.

Fall verification also may be made by human inspection of captured images. For example, following the detection of a potential fall event, an image or successive images captured proximal to the fall may be sent to the monitoring center for human verification. Image capture also may be triggered post fall (e.g., by a monitoring center or by other caregivers) to verify a fall event. Other contextual sensor or meta-data may be forwarded to human responders to assist in the verification of fall.

Fall verification procedures may be staged sequentially or paired with fall detection mechanisms to create a hierarchical fall escalation process. For example, less accurate fall detection methods may trigger less invasive user verification (e.g., prompted user button press). If no user response is given within a threshold period of time, then more accurate fall detection methods may be employed alongside more invasive fall verification (e.g., two way communications with monitoring center).

The system 400 performs fall risk assessment (740). Assessment of fall risk may be made on the basis of data captured by sensors, user interface devices, or historic and stored data. Measures such as gait speed and balance can be directly assessed via passive and user interface devices. For example, two motion sensors placed in a hallway can measure gait speed and balance can be assessed via an on-body user interface device (e.g., via on-board inertial sensor and angular rate sensor). Other behavioral data such as medication adherence, sleep patterns, kitchen or restroom use can be used to augment mobility metrics. Data can be combined with prior knowledge of fall incidents or previously verified fall events. In addition, users may be prompted to submit responses to questions or requests for information (e.g., via a user interface device or website, electronic medical records, residence layout, etc.) to form an aggregate fall risk assessment score. Scores can be computed, compared, or modified against individual or population scores and histories. Scores can also be computed for various timescales and locations. Fall risk assessment may also take into consideration trending of scores for an individual.

The system 400 performs fall risk reduction (750). Various assistive approaches may be employed with or without prior fall risk assessment scoring to help reduce fall risk. Assistance devices such as automated lighting or medication dispensers can be used to reduce environmental hazards or behaviors related to increase in fall risk, respectively. Assistance devices may be triggered by fall assessment scores, other sensors, user interface devices, or remote servers. For example, automated lighting can be turned-on when a user gets out of bed.

Furthermore, notifications or educational material can be delivered (e.g., by default, for certain fall risk assessment scores, for certain events, etc.) to the user (e.g., via a user interface device or other output device) to help the user better understand and correct fall risk factors. Tips or behavior change techniques can help the user set up a safer environment or promote behaviors associated with decreased fall risk. Notifications may be combined with sensing or other user interface prompts (e.g., prompts to answer questionnaires) to assess adherence to fall risk reduction techniques in real-time or across a period of time. Users may be scored on their ability to reduce fall risk at various timescales or in various locations. Fall risk reduction scores may be compared to individual or population historic data.

The system 400 performs reporting (760). Fall risk, detection, and prevention data, scores, annotations, or observations can be stored at the remote server. Data can be compiled and reported to users, caregivers, monitoring centers, or other trusted parties. Data (including timestamps, scores, locations, confidence, etc.) can be used for the purposes of response to events, for preventative fall risk reduction strategies, or by professional caregivers for general health assessment. Data or scores can be compared to individual or population data and reported to all aforementioned parties when appropriate. Data reporting may be combined with prompts for data entry. For example, a user could receive a notification that bathroom habits are abnormal and be asked whether they are feeling well. Access to reported data can be restricted based on preferences of the user or caregivers. Notifications, reminders, user prompts, questionnaires, monitored responses, and other user interface modes can be configured by rules with associated parameters. Rules can be stored and executed at the remote server, gateway device, sensors, or user interface devices.

Figure 8:
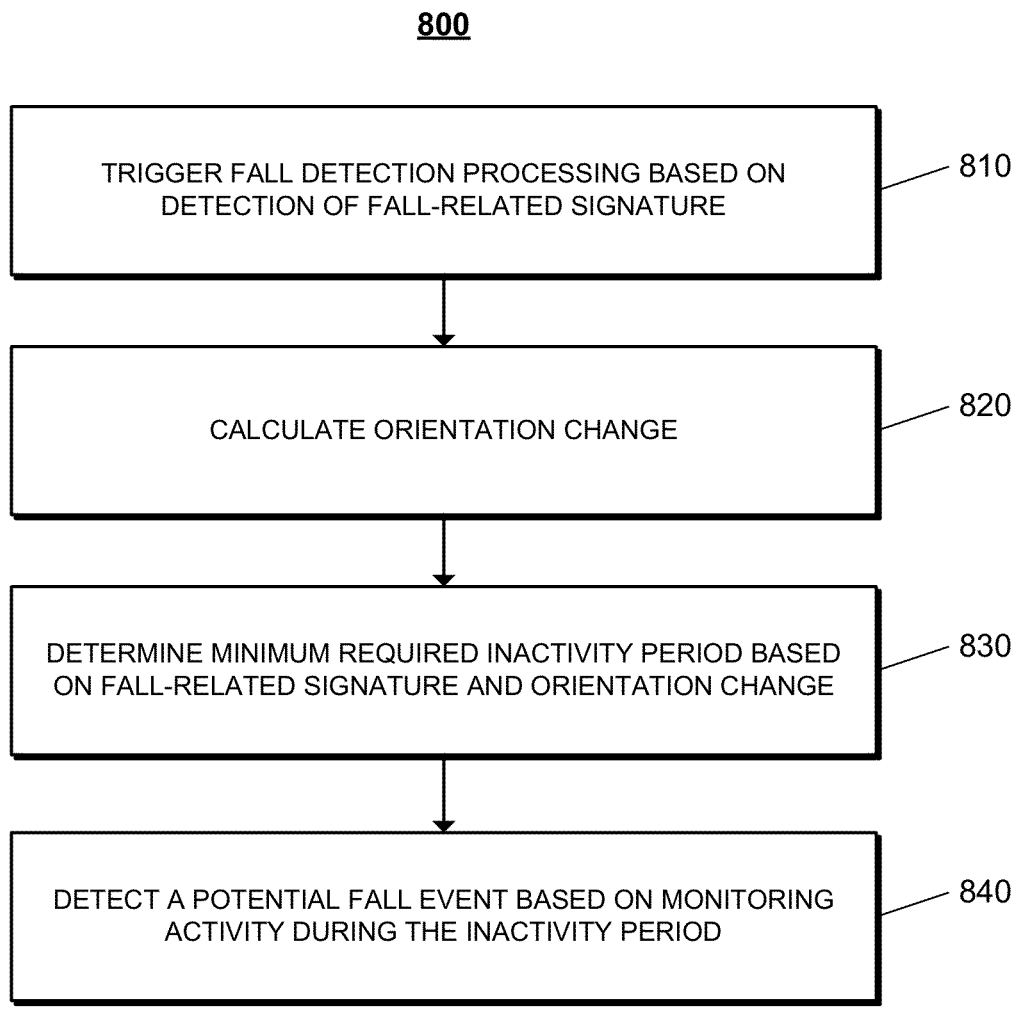

FIG. 8 illustrates an example process 800 for fall detection using an on-body user interface device. The operations of the example process 800 are described generally as being performed by the system 400. The operations of the example process 800 may be performed by one of the components of the system 400 or may be performed by any combination of the components of the system 400. The operations of the example process 800 also may be performed by one of the components of the system 200 or may be performed by any combination of the components of the system 200. In some implementations, operations of the example process 800 may be performed by one or more processors included in one or more electronic devices.

In order to accurately detect a fall event, the on-body user interface device identifies the various characteristics of a fall comprised of the user starting from a standing or sitting position, falling through to the ground, impacting a surface, and remaining inactive after the fall. The user's trunk may transition from a vertical to horizontal position. This may result in a ninety degree change in trunk orientation, but since the user may not be standing straight before the fall, or may not be prone or supine after the fall, the angle may not reach ninety degrees. FIG. 8 illustrates a fall detection process 800 for users wearing an on-body sensor with continuous sensing and detection.

The system 400 triggers fall detection processing based on detection of a fall-related signature (810). The fall detection process may be triggered by an impact metric (e.g., measured from inertial sensing) or a similar fall-related signature (e.g., free fall) crossing a minimum threshold. The fall-related signature may be quantified and stratified into defined ranges indicative of fall detection confidence.

Figure 9:
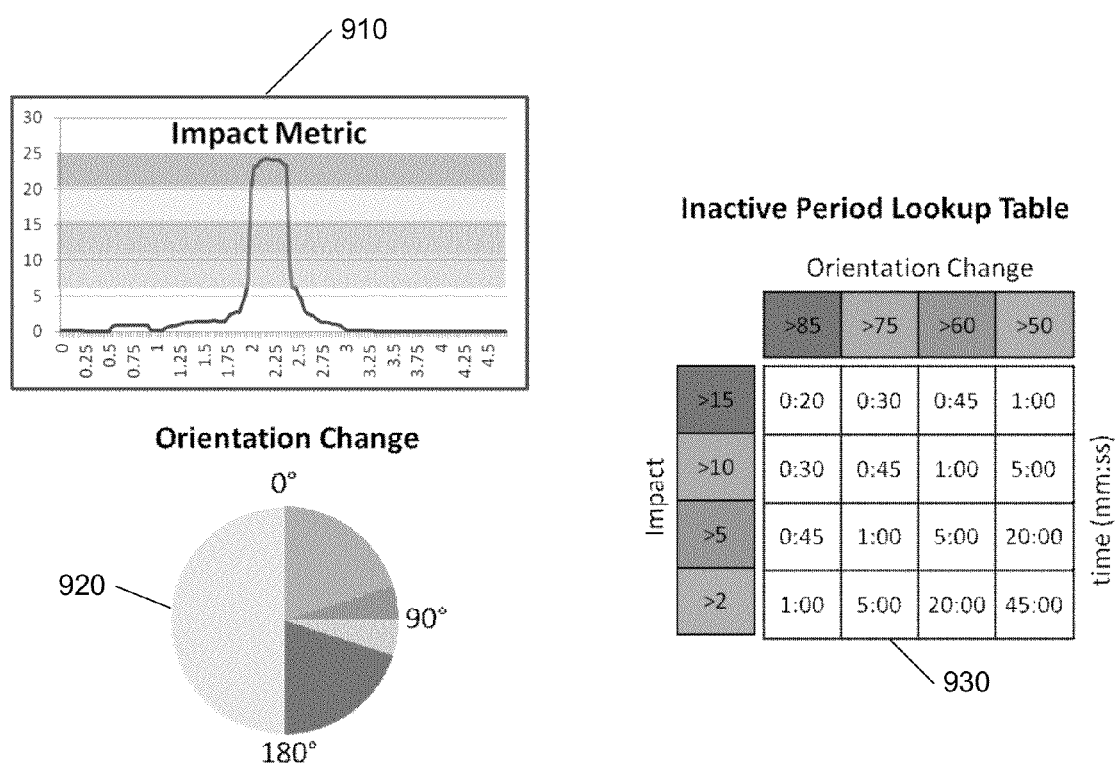
FIG. 9 is illustrates example fall detection criteria.

For instance, FIG. 9 illustrates example fall detection criteria. The fall detection criteria include a range of impact metrics 910 used to quantify a measured impact metric. As shown, the range of impact metrics may include less than two, between two to five, between five to ten, between ten to fifteen, and greater than fifteen. The system 400 may use the impact metric of two as a threshold for triggering fall detection processing. For instance, the system 400 quantifies a measured impact within the ranges of impact metrics and determines not to trigger fall detection processing based on the measured impact falling within the range of less than two. For any of the other ranges, the system 400 triggers fall detection processing and records the range in which the measured impact falls for later processing.

Referring again to FIG. 8, the system 400 calculates orientation change based on triggering fall detection processing (820). Based on the system 400 detecting that a measured impact or similar metric crosses the previously mentioned minimum threshold, the system 400 calculates an orientation change using inertial or angular rate measures from before and after the detected impact or other event. The orientation value may be quantified and stratified into defined ranges.

For example, the fall detection criteria shown in FIG. 9 include a range of orientation changes 920 used to quantify an orientation change. As shown, the range of orientation changes may include less than fifty, between fifty to sixty, between sixty to seventy-five, between seventy-five to eighty-five, and greater than eighty-five. The system 400 may use the orientation change of fifty as a threshold for continuing fall detection processing. For instance, the system 400 quantifies a calculated orientation change within the ranges of orientation changes and determines not to continue fall detection processing based on the calculated orientation change falling within the range of less than fifty. For any of the other ranges, the system 400 continues fall detection processing and records the range in which the calculated orientation change falls for later processing.

Referring again to FIG. 8, the system 400 determines a minimum required inactivity period based on the fall-related signature and the orientation change (830). Based on the defined ranges derived from impact/signature scoring and orientation scoring, a minimum required inactivity period can be determined by a lookup table or functional relationship.

The fall detection criteria shown in FIG. 9 include an inactivity period lookup table 930. The system 400 references the lookup table 930 using the range of the measured impact and the range of the calculated orientation change and sets the minimum required inactivity period as the period of time defined by the appropriate entry in the lookup table 930. For example, with an impact metric greater than ten, but less than fifteen, and an orientation change greater than eighty-five, the inactivity period is set as low as thirty seconds to signal a likely fall.

Referring again to FIG. 8, the system 400 detects a potential fall event based on monitoring activity during the minimum required inactivity period (840). The system 400 may monitor output of the on-body sensor and output from any of the other sensors in the system 400 and determine whether any of the sensors signal activity. The system 400 continues to monitor the sensor output until the set period of inactivity has been reached and the system 400 detects a potential fall event based on determining that the set period of inactivity has passed without detecting sensed activity from any of the sensors in the system 400.

Figure 10:
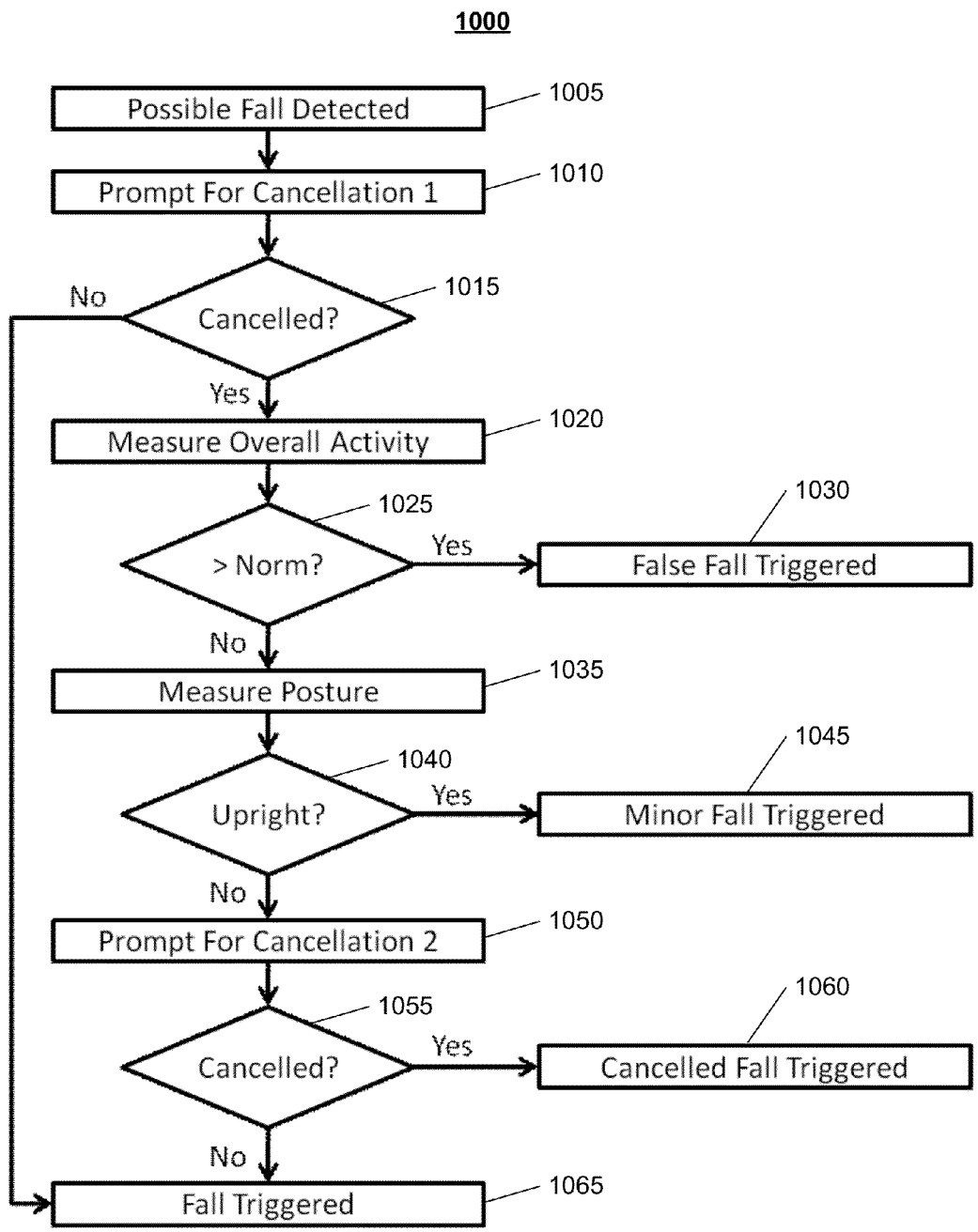

FIG. 10 illustrates an example process 1000 for tuning sensitivity and specificity of fall detection. The operations of the example process 1000 are described generally as being performed by the system 400. The operations of the example process 1000 may be performed by one of the components of the system 400 or may be performed by any combination of the components of the system 400. The operations of the example process 1000 also may be performed by one of the components of the system 200 or may be performed by any combination of the components of the system 200. In some implementations, operations of the example process 1000 may be performed by one or more processors included in one or more electronic devices.

To tune sensitivity and specificity of fall detection (e.g., the on-body fall detection process 800), the process 1000 uses user feedback. The process 1000 may produce more granular fall reporting (e.g., true, false, minor, canceled falls) and may help to reduce and report incidence of false positives or false negatives.

The system 400 detects a potential fall event (1005). A possible fall is detected by the on-body device, by other sensors, or user interface devices. Any of the techniques described throughout this disclosure may be used to detect a potential fall event.

The system 400 prompts the user for cancellation of the potential fall event (1010). A user prompt may be initiated (e.g., audible or visual). The user can respond (e.g., by a button press or vocalization) to the user prompt at the device to cancel the detected potential fall event.

The system 400 determines whether the user cancels the potential fall event within a defined period of time (1015). For instance, the system 400 monitors for input cancelling the potential fall event until the defined period of time has been reached and the system 400 determines whether the user cancelled the potential fall event within the defined period of time based on the monitoring. Based on a determination that the potential fall event was not cancelled within the defined period of time, the system 400 generates a fall signal (e.g., a fall signal from the body-worn device).

Based on a determination that the potential fall event was cancelled within the defined period of time, the system 400 makes a measurement of overall activity over the minimum inactivity period previously mentioned (1020). For example, the system 400 measures the activity detected by the on-body sensor after detection of the potential fall event until the input cancelling the potential fall event was received.

The system 400 determines whether the measurement of overall activity meets an expected maximum activity (1025).

For instance, the system 400 compares the measurement of overall activity to the expected maximum activity and determines whether the measurement of overall activity meets the expected maximum activity based on the comparison.

Based on a determination that the measurement of overall activity meets the expected maximum activity, the system 400 signals a false fall detection (1030). For example, the system 400 classifies the sensor data used to detect the potential fall event as being sensor data associated with a false detection of a potential fall event. In this example, the system 400 may tune the potential fall detection process such that sensor data similar to the sensor data associated with the false detection of the potential fall event does not result in detection of a potential fall event in the future.

Based on a determination that the measurement of overall activity does not meet the expected maximum activity, the system 400 measures posture or orientation (1035) and determines whether the subject recovered from the suspected fall based on the measured posture or orientation (1040). For instance, the system 400 analyzes the measured posture or orientation and determines whether the subject has returned to an upright position.

Based on a determination that the subject recovered from the suspected fall, the system 400 triggers a minor fall (1045). For example, the system 400 classifies the sensor data used to detect the potential fall event as being sensor data associated with a minor fall. In this example, the system 400 may tune the potential fall detection process such that sensor data similar to the sensor data associated with the minor fall results in detection of a minor fall event in the future. The system 400 may handle minor fall events differently than regular fall events. For instance, the system 400 may wait longer to see if a patient recovers from a minor fall prior to alerting a remote caregiver or monitoring station.

Based on a determination that the subject did not recover from the suspected fall, the system 400 performs another user prompt for cancellation (1050) and determines whether the user cancels the potential fall event within a defined period of time from the additional prompt for cancellation (1055). Based on a determination that the potential fall event was cancelled within the defined period of time, the system 400 signals a cancelled fall (1060). For instance, the system 400 does not provide an alert for the potential fall event, but does classify the sensor data used to detect the potential fall event as being sensor data associated with a fall that was ultimately cancelled.

Based on a determination that the potential fall event was not cancelled within the defined period of time, the system 400 generates a fall signal (1065). For instance, the system 400 may generate a fall signal from the body-worn device. The fall signal may be sent to a remote caregiver or monitoring station to alert the remote caregiver or monitoring station to provide assistance to the patient who experienced the potential fall event.

Granular fall detection classes such as true fall, false fall, minor fall, and cancelled fall can be used to tune system parameters for each individual user, provide caregivers or trusted individuals with fall data, and provide automated mechanisms for fall verification. Furthermore, the data can be stored at the remote servers.

Figure 11:
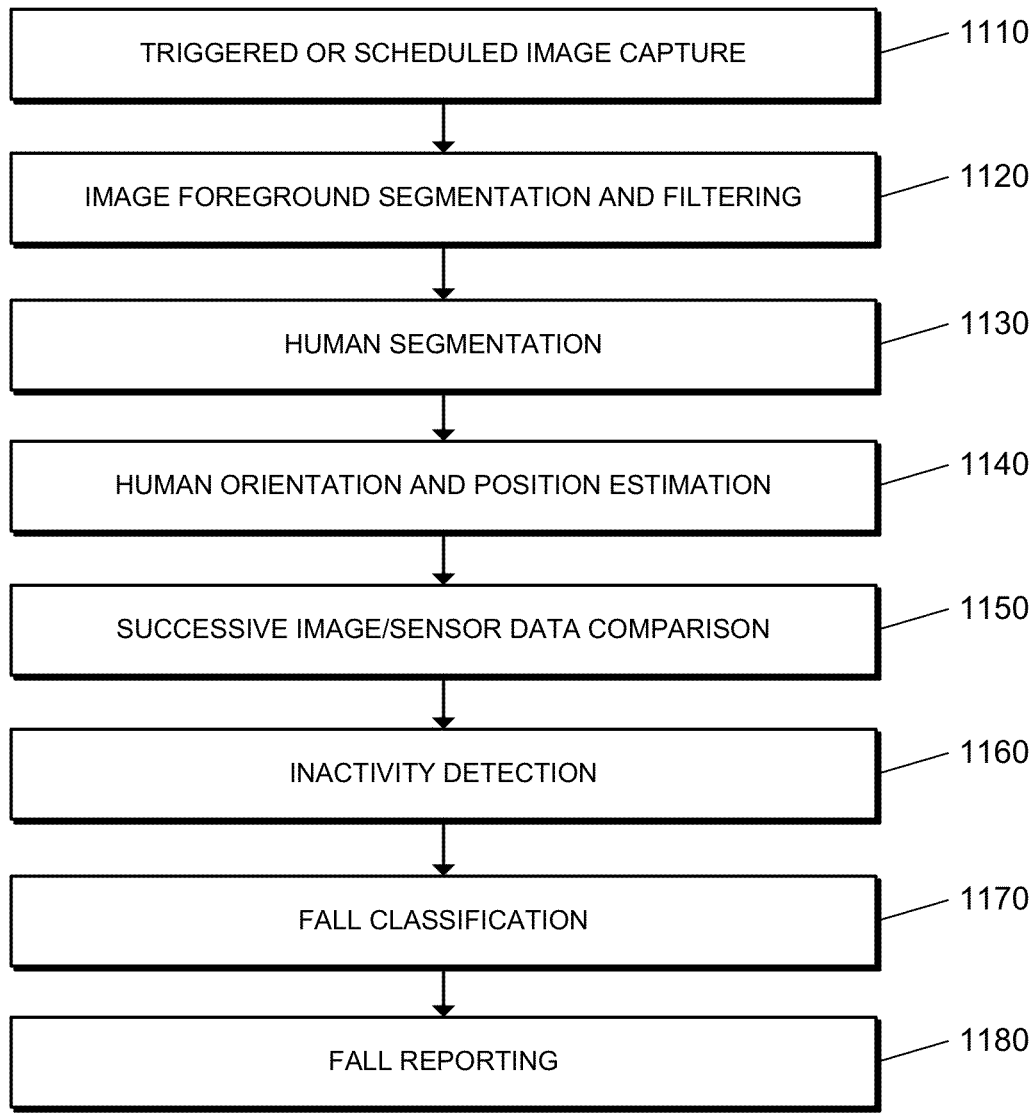

FIG. 11 illustrates an example process 1100 for fall detection and reporting. The operations of the example process 1100 are described generally as being performed by the system 400. The operations of the example process 1100 may be performed by one of the components of the system 400 or may be performed by any combination of the components of the system 400. The operations of the example process 1100 also may be performed by one of the components of the system 200 or may be performed by any combination of the components of the system 200. In some implementations, operations of the example process 1100 may be performed by one or more processors included in one or more electronic devices.

In general, the process 1100 enables fall detection and reporting based on human movement analysis. The system 400 performs a triggered or scheduled image capture (1110). For example, the system 400 may trigger a camera on an image sensing device to capture an image based on events detected by one or more of the image sensing device's sensors (e.g., perceived motion passive infrared motion sensor, tri-axial inertial sensor). In this example, movement or impact detected proximal to the image sensing device may initiate the capture of an image. Furthermore, the system 400 may trigger the camera by one or more external sensors interfaced via a gateway device. For instance, the press of a panic button or the opening of a door sensor may trigger one or more image sensing devices to capture an image. Finally, image capture may be scheduled (e.g., capture an image every one minute during the hours of six in the morning through ten in the evening). In lower light conditions (e.g., characterized by the illumination sensor), the system 400 may employ infrared illumination to increase image detail and quality.

After image capture, the system 400 performs image foreground segmentation and filtering (1120). The system 400 (e.g., the image sensing device) may perform image foreground segmentation via background subtraction or other averaging approaches. The system 400 may filter captured images to help reduce foreground noise and isolate large regions of change. The process may identify changed pixels from previous images, including those morphologically likely to represent human forms or shapes.

After image foreground segmentation and filtering, the system 400 performs human segmentation (1130). The system 400 segments possible human shapes via template matches, shape fitting, or similar methods. For example, the system 400 may segment a foreground shape falling within an approximate elliptical boundary over a size threshold. Such segmentation may reduce incidence of false detection and reporting (e.g., small pet activity). To further reduce incidence of false detection and reporting, the system 400 may remove regions of the camera's field of view from analysis. For instance, if a bed were present in the field of view, the bed may be marked as a non-detection region and the system 400 would not analyze that portion of images captured by the image sensing device.

After human segmentation, the system 400 performs human orientation and position estimation (1140). For example, the system 400 calculates orientation (e.g., human shape upright, angled, prone, etc.) and position (e.g., human shape above floor, near floor, etc.) by template or boundary shape proportion and rotation relative to a horizontal image plane. This estimation enables identification of postures and resting positions indicative of a fall. The floor proximal planar boundary can be specifically defined and moved to fit the unique geometries of different rooms.

After human orientation and position estimation, the system 400 performs successive image and/or sensor data comparison (1150). For example, the system 400 stores, either on or off the image sensing device, the orientation and position information calculated previously and compares the prior orientation and position information with successive image orientations and positions. The system 200 repeats this process and isolates changes in position and orientation indicative of a fall (e.g., movement towards the ground), or relative stasis of position and orientation indicative of a fall (e.g., incapacitation after a fall). Furthermore, the system 400 combines motion sensor information with or used independent of image-based analysis to ascertain movement through horizontal planes of motion (e.g., human falling from an upright position).

The system 200 performs inactivity detection (1160). For example, the system 400 detects periods of relative inactivity, such as those following a potential fall, from lack of or decreased motion, inertial measures, image-derived orientation and position information, external sensors, or even a combination thereof. The system 400 may classify longer periods of relative inactivity as being indicative of a fall, and classify shorter periods of relative inactivity as being indicative of a non-fall event or recovery from a fall.

After inactivity detection, the system 400 performs fall classification (1170). The system 400 may combine (e.g., logically or algebraically) the data and information compiled in previous operations of the process 1100 and use the combined data in several ways to classify possible falls. For example, if an impact is detected, orientation and position are indicative of a human in a fallen state, and a period of inactivity has exceeded a defined threshold, then the system 400 classifies the event as a fall. Classification sensitivity may be configured by the user based on manipulation of variables associated with any of the aforementioned steps. For example, fall sensitivity could be set by adjusting the interval of sensed inactivity or the threshold for decreased activity. Not all prior conditions must be met, nor all prior steps completed, for fall classification. The system 400 may report classification confidence based on the quality of inputs or classifier performance. Furthermore, the system 400 may implement the classifier in a variety of ways such as, but not limited to an expert system, native Bayes, decision tree, neural network, etc.

After fall classification, the system 400 performs fall reporting (1180). For example, potential fall events are forwarded to a gateway device, remote monitoring servers, and ultimately to users or central monitoring station(s) if appropriate rules and preferences are met. Images (e.g., past and present), data, and location information can be sent for purposes of reporting and verification. Moreover, potential non-fall events, images, data, and location can be forwarded to users or central monitoring station(s) for verification. Verification of fall events is not a requisite function of the system, rather an additional feature. Fall detection can be performed with or without image or other human-based verification.

Figure 12:
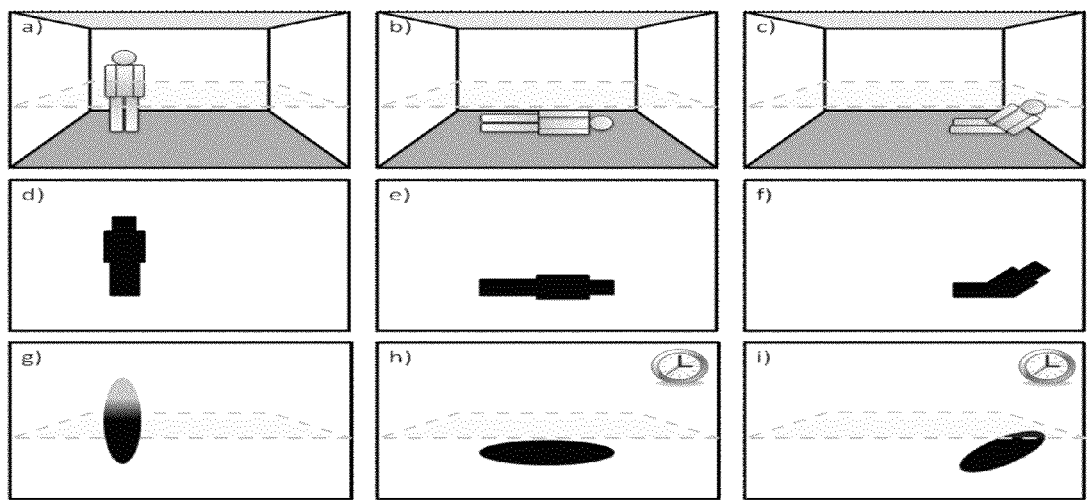
FIG. 12 is a diagram illustrating fall detection examples.

FIG. 12 shows fall detection examples with three possible scenarios that illustrate aspects of the fall detection process 1000 discussed above. In the first scenario (a), a person stands upright in a room. In the second scenario (b), a person has fallen and is prone on the floor. In the third scenario (c), a person has fallen to a slumped position on the floor. Illustrations (d), (e), and (f) represent the results of foreground separation and filtering of illustrations (a), (b), and (c), respectively. Illustrations (g), (h), and (i) represent the results of human orientation and position estimation and inactivity detection (as denoted by a clock) of the previous illustrations, respectively. Notice in illustration (g) that the human shape estimator, illustrated as an ellipse, but not limited to ellipses, extends beyond a floor proximal planar boundary; whereas in illustrations (h) and (i), the human shape estimators are below the plane and their orientations are not vertical, hence, inactivity detection has commenced.

Analysis of room geometry within captured images may be used to project a virtual plane of where a person should be oriented below in a fall event. The system 400 may analyze floor geometry and then perform centroid-based processing to determine where the floor is located in the captured images. After determining the location of the floor, the system 400 projects the virtual plane within the captured images at a particular distance above the floor.

In some implementations, the image sensing device and optional trigger sources (e.g., other sensors) communicate to a gateway (e.g., home monitoring panel) within a home or facility. The gateway's memory enables buffering of images and data from the image sensor and other sensors. Data is forwarded to remote monitoring servers over a long range wireless network (e.g., cellular link). Rules and preferences set at the remote monitoring server enable potential fall information (e.g., captured images and data) to be forwarded via an IP network to users or a central monitoring station for fall verification. If a fall is verified by human inspection of captured images and data, a response can be initiated (e.g., a two-way voice call may be established with the gateway device, emergency responders may be dispatched, etc.) and location information from the system can be communicated to those providing assistance.

In some implementations, the system (e.g., the system 200 or the system 400) may evaluate context in determining how to handle a fall detection event. In these implementations, the system may check other activity in the property and determine how to handle the fall detection event based on the other activity. For instance, when the system detects other activity in the property, the system may attempt to alert someone in the property to the potential fall event (e.g., by providing an audible alert in the home that indicates the fall detection event). When the system does not detect other activity in the property, the system may, based on the fall detection event, send electronic messages to a caregiver associated with the property to alert the caregiver to the fall detection event, establish a two-way voice communication session with a monitoring system at the property, and/or dispatch emergency services.

In some examples, the system may tune sensitivity of one or more sensors/contexts used in fall detection and may determine a score as part of fall classification. In these examples, the system may determine the score based on a number of sensors that indicate a potential fall. For instance, the system may determine a relatively high score when the system detects a thud based on an accelerometer sensor, detects multiple motion sensors indicating motion consistent with a fall, and performs image analysis that suggests that a person has moved from a vertical orientation to a horizontal orientation below a plane near the floor. The system may determine a relatively low score when the system only performs image analysis that suggests that a person is horizontally oriented below a plane near the floor. The system may consider the number of motion sensors detecting motion and leverage all sensor data. The system may typically operate using a subset of sensors and move to a process that leverages all sensors when a potential fall is detected by the subset of sensors. The system may consider historic data (e.g., classification by caregivers of whether a fall detection event was actually a fall or a mistake) and tune fall detection based on the historic data.

In some implementations, the location in the home where the fall occurred may be determined and communicated to an emergency response team. In addition, the location in the home where the fall occurred may be used to pick the other sensors the system reviews in confirming a potential fall event. For instance, when the system determines that the potential fall occurs in the basement, the system determines not to consider sensors in the upstairs bedroom, as the sensors in the upstairs bedroom are unlikely to be relevant to the potential fall event in the basement.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A method comprising:
    monitoring output from at least one sensor configured to sense activity associated with a patient falling;
    analyzing the monitored output from the at least one sensor over a period of time to determine activities of the patient over the period of time;
    accessing information indicative of expected activities of the patient over the period of time;
    comparing the determined activities of the patient over the period of time to the expected activities of the patient over the period of time;
    based on the comparison revealing that the determined activities of the patient over the period of time do not match the expected activities of the patient over the period of time, determining, by at least one processor, a level of fall risk associated with the patient; and
    performing an operation directed to assisting the patient with a fall event based on the determined level of fall risk associated with the patient.

2. The method of claim 1, wherein performing the operation directed to assisting the patient with a fall event based on the determined level of fall risk associated with the patient comprises:
    determining that the level of fall risk associated with the patient exceeds a threshold; and
    based on the determination that the level of fall risk associated with the patient exceeds the threshold, sending a message to a monitoring server.

3. The method of claim 1, wherein performing the operation directed to assisting the patient with a fall event based on the determined level of fall risk associated with the patient comprises:
    determining that the level of fall risk associated with the patient exceeds a threshold; and
    based on the determination that the level of fall risk associated with the patient exceeds the threshold, automatically performing one or more operations to reduce the level of fall risk associated with the patient.

4. The method of claim 1:
    wherein analyzing the monitored output from the at least one sensor over a period of time to determine activities of the patient over the period of time comprises measuring gait speed and balance via passive and user interface devices; and
    wherein determining the level of fall risk associated with the patient comprises determining the level of fall risk based on the measured gait speed and balance.

5. The method of claim 4, wherein measuring gait speed and balance via passive and user interface devices comprises:
    measuring gait speed based on output of at least two motion sensors; and
    measuring balance via an on-body user interface device.

6. The method of claim 1, wherein determining the level of fall risk associated with the patient comprises augmenting mobility metrics with adherence, sleep patterns, kitchen and restroom use.

7. The method of claim 1, wherein determining the level of fall risk associated with the patient comprises:
    computing fall risk assessment scores for the patient for various timescales and locations; and
    accounting for trending of the fall risk assessment scores for the patient.

8. The method of claim 1, wherein performing the operation directed to assisting the patient with a fall event based on the determined level of fall risk associated with the patient comprises controlling automated lighting to reduce environmental hazards.

9. The method of claim 1, wherein the at least one sensor configured to sense activity associated with the patient falling is an on-body sensor configured to detect an impact and determine a change in an orientation of the patient.

10. The method of claim 1, wherein the at least one sensor configured to sense activity associated with the patient falling is a sensor configured to determine a presence of the patient in the room.

11. A system comprising:
    at least one processor; and
    at least one memory coupled to the at least one processor having stored thereon instructions which, when executed by the at least one processor, causes the at least one processor to perform operations comprising:
        monitoring output from at least one sensor configured to sense activity associated with a patient falling;
        analyzing the monitored output from the at least one sensor over a period of time to determine activities of the patient over the period of time;

accessing information indicative of expected activities of the patient over the period of time;

comparing the determined activities of the patient over the period of time to the expected activities of the patient over the period of time;

based on the comparison revealing that the determined activities of the patient over the period of time do not match the expected activities of the patient over the period of time, determining a level of fall risk associated with the patient; and performing an operation directed to assisting the patient with a fall event based on the determined level of fall risk associated with the patient.

12. The system of claim 11, wherein performing the operation directed to assisting the patient with a fall event based on the determined level of fall risk associated with the patient comprises:

determining that the level of fall risk associated with the patient exceeds a threshold; and based on the determination that the level of fall risk associated with the patient exceeds the threshold, sending a message to a monitoring server.

13. The system of claim 11, wherein performing the operation directed to assisting the patient with a fall event based on the determined level of fall risk associated with the patient comprises:

determining that the level of fall risk associated with the patient exceeds a threshold; and based on the determination that the level of fall risk associated with the patient exceeds the threshold, automatically performing one or more operations to reduce the level of fall risk associated with the patient.

14. The system of claim 11:

wherein analyzing the monitored output from the at least one sensor over a period of time to determine activities of the patient over the period of time comprises measuring gait speed and balance via passive and user interface devices; and wherein determining the level of fall risk associated with the patient comprises determining the level of fall risk based on the measured gait speed and balance.

15. The system of claim 14, wherein measuring gait speed and balance via passive and user interface devices comprises:

measuring gait speed based on output of at least two motion sensors; and measuring balance via an on-body user interface device.

16. The system of claim 11, wherein determining the level of fall risk associated with the patient comprises augmenting mobility metrics with adherence, sleep patterns, kitchen and restroom use.

17. The system of claim 11, wherein determining the level of fall risk associated with the patient comprises:

computing fall risk assessment scores for the patient for various timescales and locations; and accounting for trending of the fall risk assessment scores for the patient.

18. The system of claim 11, wherein performing the operation directed to assisting the patient with a fall event based on the determined level of fall risk associated with the patient comprises controlling automated lighting to reduce environmental hazards.

19. The system of claim 11, wherein the at least one sensor configured to sense activity associated with the patient falling is an on-body sensor configured to detect an impact and determine a change in an orientation of the patient.

20. The system of claim 11, wherein the at least one sensor configured to sense activity associated with the patient falling is a sensor configured to determine a presence of the patient in the room.

* * * * *